(12) United States Patent
Myung Bae et al.

(10) Patent No.: US 7,687,683 B2
(45) Date of Patent: Mar. 30, 2010

(54) SWEETPOTATO EXPANSIN CDNA AND HIGH-YIELD TRANSGENIC PLANTS USING THE SAME

(75) Inventors: Jung Myung Bae, Seoul (KR); Seol Ah Noh, Seoul (KR); Sun-Hee Park, Seoul (KR); Man Sup Kwak, Seoul (KR); Jeong Sheop Shin, Seoul (KR); Kyung Hee Paek, Seoul (KR)

(73) Assignee: Korea University Industry and Academy Corporation Foundation, Seoul (KR)

(*) Notice: Subject to any disclaimer, the term of this patent is extended or adjusted under 35 U.S.C. 154(b) by 165 days.

(21) Appl. No.: 11/694,367

(22) Filed: Mar. 30, 2007

(65) Prior Publication Data

US 2007/0283457 A1    Dec. 6, 2007

(30) Foreign Application Priority Data

Jun. 1, 2006    (KR) ............. 10-2006-0049596

(51) Int. Cl.
C12N 15/82 (2006.01)
C12N 15/29 (2006.01)
A01H 5/00 (2006.01)

(52) U.S. Cl. ............ 800/298; 536/23.6; 435/320.1; 435/252.3

(58) Field of Classification Search .......... None
See application file for complete search history.

(56) References Cited

FOREIGN PATENT DOCUMENTS

| KR | 20040084186 B1 | 10/2004 |
|---|---|---|
| KR | 10 2004 10110944 A | 12/2004 |
| KR | 20040110944 A | 12/2004 |
| WO | 03 086066 A2 | 10/2002 |
| WO | 02086066 A2 | 10/2002 |
| WO | 2006057527 A1 | 6/2006 |

OTHER PUBLICATIONS

Alexandrov N.N. et al. Features of Arabidopsis genes and genome discovered using full-length cDNAs. Plant Mol Biol. Jan. 2006;60(1):69-85.*
Rochange S.F. et al. Expression of a heterologous expansin in transgenic tomato plants. Planta. Sep. 2000;211(4):583-6.*
Shcherban T. et al. GenBank Accession U30382, Apr. 23, 2004.*
You M.K. et al. Identification of genes possibly related to storage root induction in sweet potato. FEBS Letters 536 (2003) 101-105.*
Otani M. et al. Production of Herbicide-Resistant Sweetpotato (*Ipomoea batatas* (L.) Lam.) Plants by Agrobacterium tumefaciens-mediated Transformation. Breed. Sci. vol. 53: 145-148. (2003).*
Kwak M.S. et al. Two sweetpotato ADP-glucose pyrophosphorylase isoforms are regulated antagonistically in response to sucrose content in storage roots. Gene. Jan. 17, 2006;366(1):87-96. Epub Dec. 7, 2005.*
Genbank Accession No. DQ 100330, Jul. 18, 2005.

\* cited by examiner

*Primary Examiner*—Cynthia Collins
(74) *Attorney, Agent, or Firm*—Sughrue Mion, PLLC

(57) ABSTRACT

Disclosed herein are a sweetpotato expansin cDNA (IbExpansin), a plant transformation vector carrying the same, and a transgenic plant comprising the vector. The transgenic *Arabidopsis*, prepared using the IbExpansin cDNA, outgrows the wild-type, thereby increasing in size and seed production up to three times. Thus, the gene is useful in the generation of highly productive transgenic plants for improvement in biomass and/or seed production.

8 Claims, 14 Drawing Sheets

(5 of 14 Drawing Sheet(s) Filed in Color)

FIG. 4

```
SEQ ID NO: 12   PcExpansin : ---------MKMAIAYGFCLVGLLALVSCAHAYGGGWVNARATFYGGGDASGTMGGACG :  51
SEQ ID NO: 13   PpExpansin : ---------MKMAIAYGFCLVGLLALVSCAHAYGGGWVNARATFYGGGDASGTMGGACG :  51
SEQ ID NO: 14   PaExpansin : ---------MKMAIAYGFCLVGLLALVSCAHAYGGGWVDARATFYGGSDASGTMGGACG :  51
SEQ ID NO: 15   CaExpansin : ------------MALLG-LLLMGISLMFQSVHGYGG--WINAIATFYGGGDASGTMGGACG :  46
SEQ ID NO: 16   LeExpansin : ------------MALLA-ILLMGISLMFQSAHGYGG--WINAIATFYGGGDASGTMGGACG :  46
SEQ ID NO: 17   IbExpansin : HSSTNSTEAITMAVLE-LLLVGVLATLSPVHGYWG--WSSARATFYGGGDASGTMGGACG :  57

PcExpansin : YGNLYSQGYGTNTAALSTALFNNGLGCGSCYEIRCVNDPKVCLPGAIVVIATNFCPPNNA : 111
                PpExpansin : YGNLYSQGYGTNTAALSTALFNNGLGCGSCYEIRCVSDPKVCLPGAIVVIATNFCPPNNA : 111
                PaExpansin : YGNLYSQGYGTNTAALSTALFNNGLGCGSCYEIRCVNDPKVCLPGAIVVIATNFCPPNNA : 111
                CaExpansin : YGNLYSSGYGTNTAALSTALFNNGLSCGQCFQLMCVRARQVCLPGIITVIATNFCPP--- : 103
                LeExpansin : YGNLYSTGYGTNTAALSTALFNNGLSCGACFQLMCVNAGQYCLPGIITVIATNFCPP--- : 103
                IbExpansin : YGNLYSSGYGTNTAALSTALFNNGLSCGSCFQIRCVND-RSCLRGVITVIATNFCPP--- : 113

PcExpansin : LPNNAGGWCNPPQHHFDLSQPVEQHIAQYKAGVVPVAYRRVPCRRRGGIRFTINGHSYFN : 171
                PpExpansin : LPNNAGGWCNPPQHHFDLSQPVEQHIAQYKAGVVPVAYRRVPCRRRGGIRFTINGHSYFN : 171
                PaExpansin : LPNNAGGWCNPPQHHFDLSQPVEQHIAQYKAGVVPVAYRRVPCRRRGGIRFTINGHSYFN : 171
                CaExpansin : -----GGWCDPPNHHFDLSQPIFLRIAQYRAGIVPVAYRRVPCRRRGGIRFTINGHSYFN : 158
                LeExpansin : -----GGWCDPPRPHFDLSQPIFLRIAQYRAGIVPVAYRRVPCRRSGGIRFTINGHSYFN : 158
                IbExpansin : -----GGWCEPPNPHFDLSQPVFLRIAQYRAGVVPVAYRRVPCRRSGGIRFTINGHAFFN : 168

PcExpansin : LVLITNVGGAGDVHSVSVKGSRTGWQAMSRNWGQNWQSRSYLNGQSLSFKVTISDGRTVV : 231
                PpExpansin : LVLITNVGGAGDVHSVSVKGSRTGWQAMSRNWGQNWQSRSYLNGQSLSFKVTISDGRTVV : 231
                PaExpansin : LVLITNVGGAGDVHSVSVKGSRTGWQAMSRNWGQNWQSRSYLNGQSLSFKVTISDGRTVV : 231
                CaExpansin : LVLVTNVGGSGDVHSVYIKGSRTQWQEMSRNWGQNWQMAYLNGQSLSFKVTIGDGRTVV : 218
                LeExpansin : LVLVTNVGGSGDVHSVYIKGSRTQWQEMSRNWGQNWQMAYLNGQSLSFKVTIGDGRTVV : 218
                IbExpansin : LVLVTNVGGSGDVHAVYIKGSRTGWQMSRNWGQNWQSANLNGQSLSFKVTGDSRSVV : 228

PcExpansin : AYNAAPAGWSFGQTYSGAQER : 252
                PpExpansin : SYNAAPAGWSFGQTYSGAQER : 252
                PaExpansin : SYNAALAGWSFGQTYSGQLR  : 252
                CaExpansin : SYNAAPSSWSFGQTFSGQQER : 239
                LeExpansin : SYNAAPSSWSFGQTFSGQQER : 239
                IbExpansin : SYNAAPPGWSFGQTYSGAQER : 249
```

PcExpansin – 'Prunus cerasus'  
PpExpansin – 'Prunus persica'  
PaExpansin – 'Prunus avium'  
CaExpansin – 'Capsicum annuum'  
LeExpansin – 'Lycoperson esculentum'  
IbExpansin – 'Ipomoea batatas'

FIG 5

Homology among expansin amino acid sequences

| Sequence comparison | | Identity (%) |
|---|---|---|
| | | overall |
| IbExpansin | LeExpansin | 78 |
| | CaExpansin | 79 |
| | PcExpansin | 73 |
| | PaExpansin | 73 |
| | PpExpansin | 73 |

| Starch | WT | Exp-1 | Exp-4 | Exp-22 |
|---|---|---|---|---|
| ug/seed | 0.98±0.06 | 1.55±0.13 | 1.48±0.03 | 1.54±0.06 |

Fig 15

Seed Production of Transgenic IbExpansin-Arabidopsis

| Genotype | Seed weight[1] | Seed number per silique | Silique number per plant | Total seed number | Total seed weight, mg |
|---|---|---|---|---|---|
| Wild type | 14.25 ± 1.16 | 52.8 ± 3.34 | 199 ± 48.7 | 10,507.2 ± 162.66 | 149.73 ± 0.19 |
| Exp-4 | 22.43 ± 1.49 | 58.6 ± 4.17 | 338 ± 99.1 | 19,806.8 ± 413.25 | 444.27 ± 0.62 |

[1]Weight of seeds produced is given in mg per 1,000 seeds.

SEQUENCE LISTING

<160> NUMBER OF SEQ ID NOS: 17

<210> SEQ ID NO 1
<211> LENGTH: 1213
<212> TYPE: DNA
<213> ORGANISM: Ipomoea batatas

<400> SEQUENCE: 1

```
cattcctcta ccaattcaac tgaagcaata acaatggcgg ttcttgagct tcttctggtc      60
ggagttcttg ccacgttgtc tccggtgcat ggctactggg gctggagcag cgctcgcgcc     120
accttctacg gcggcggtga tgcttctgga acaatgggcg gagcctgcgg gtatgggaac     180
ctgtatagct caggctatgg caccaacact gcggcactta gcaccgctct gttcaacaat     240
gggctcagct gcgggtcctg tttccagata aggtgtgtga acgaccggtc ctgcctccgc     300
ggcgtaatca ccgtcaccgc caccaatttc tgcccgcccg gcggctggtg cgagcccccc     360
aacccacact tgatctctc tcagcctgtt ttcttgagaa ttgcccagta cagagccgga     420
gttgttcccg ttgcttaccg acgggtgcct tgcaggagga gtggaggaat caggttcacc     480
attaacggcc atgctttctt caacctggta ctagtaacca acgtgggagg ctccggcgac     540
gtacacgccg tgtacatcaa aggatcaaga accgggtggc aaatgatgtc cagaaactgg     600
ggccaaaact ggcagagcaa cgccaacctc aacggccaaa gcctctcatt ccgggtggtc     660
accggcgaca gccgcagcgt cgtctcctac aacgccgctc cccccggctg gtccttcggc     720
cagacctact ccggcgccca gttccgctag gccggaattc atcaaacacc cccatttttt     780
tcccgccata tatatgat ctccaaacct atacataact aaagcctaca ccatttttac      840
aagtttgaaa tgcaattaaa gtcatgggga tgggaaaatg ttgatcaagt ttccggccgc     900
cctctctcac tttttttct aaaagggatt ggttttgatc gaaagccctt ttggccatga     960
aaattggcca ttcaatcaac aagaattgaa gcagagttga agtggtagtt agttatatca    1020
agattgtgct accccatgac tagcttaatt agtactgcat tatttatgtg attattatta    1080
ttatgcagac aaaatgtgtc tgcataccta ccctgtggaa caacattaat ttttttttcc    1140
tcgtcttctt cgtcgtcgtt tgtaattagt atagcattaa ggttaaacag ctaatgctga    1200
gtgtggagac agt                                                       1213
```

<210> SEQ ID NO 2
<211> LENGTH: 238
<212> TYPE: PRT
<213> ORGANISM: Ipomoea batatas

<400> SEQUENCE: 2

```
Met Ala Val Leu Glu Leu Leu Val Gly Val Leu Ala Thr Leu Ser
 1               5                  10                  15

Pro Val His Gly Tyr Trp Gly Trp Ser Ser Ala Arg Ala Thr Phe Tyr
                20                  25                  30

Gly Gly Gly Asp Ala Ser Gly Thr Met Gly Gly Ala Cys Gly Tyr Gly
            35                  40                  45

Asn Leu Tyr Ser Ser Gly Tyr Gly Thr Asn Thr Ala Ala Leu Ser Thr
        50                  55                  60

Ala Leu Phe Asn Asn Gly Leu Ser Cys Gly Ser Cys Phe Gln Ile Arg
65                  70                  75                  80

Cys Val Asn Asp Arg Ser Cys Leu Arg Gly Val Ile Thr Val Thr Ala
                85                  90                  95

Thr Asn Phe Cys Pro Pro Gly Gly Trp Cys Glu Pro Pro Asn Pro His
            100                 105                 110

Phe Asp Leu Ser Gln Pro Val Phe Leu Arg Ile Ala Gln Tyr Arg Ala
        115                 120                 125

Gly Val Val Pro Val Ala Tyr Arg Arg Val Pro Cys Arg Arg Ser Gly
    130                 135                 140

Gly Ile Arg Phe Thr Ile Asn Gly His Ala Phe Phe Asn Leu Val Leu
145                 150                 155                 160

Val Thr Asn Val Gly Gly Ser Gly Asp Val His Ala Val Tyr Ile Lys
                165                 170                 175

Gly Ser Arg Thr Gly Trp Gln Met Met Ser Arg Asn Trp Gly Gln Asn
            180                 185                 190

Trp Gln Ser Asn Ala Asn Leu Asn Gly Gln Ser Leu Ser Phe Arg Val
        195                 200                 205

Val Thr Gly Asp Ser Arg Ser Val Val Ser Tyr Asn Ala Ala Pro Pro
    210                 215                 220

Gly Trp Ser Phe Gly Gln Thr Tyr Ser Gly Ala Gln Phe Arg
225                 230                 235
```

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggcagaaat tggtggcggg tgacggtg                                          28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acaggacccg cagctgaccc cattgttg                                          28

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtaggatccc attcctctac caattcaact gaa                                    33

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatggtacca ctgtctccac actcagcatt                                        30

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aattaaccct cactaaaggg                                                   20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgggatatca ctcagcataa tg                                                22

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctctcccgt ggtttcaagg accagatc                                          28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtctgtgagc caatcaacct tacgcctg                                          28

<210> SEQ ID NO 11

-continued

<211> LENGTH: 717
<212> TYPE: DNA
<213> ORGANISM: Ipomoea batatas

<400> SEQUENCE: 11

```
atggcggttc ttgagcttct tctggtcgga gttcttgcca cgttgtctcc ggtgcatggc      60
tactgggget ggagcagcgc tcgcgccacc ttctacggcg gcggtgatgc ttctggaaca     120
atgggcggag cctgcgggta tgggaacctg tatagctcag gctatggcac caacactgcg     180
gcacttagca ccgctctgtt caacaatggg ctcagctgcg gtcctgtttt ccagataagg     240
tgtgtgaacg accggtcctg cctccgcggc gtaatcaccg tcaccgccac caatttctgc     300
ccgcccggcg ctggtgcga gcccccaac ccacactttg atctctctca gcctgttttc      360
ttgagaattg cccagtacag agccggagtt gttcccgttg cttaccgacg ggtgccttgc     420
aggaggagtg gaggaatcag gttcaccatt aacggccatg ctttcttcaa cctggtacta     480
gtaaccaacg tgggaggctc cggcgacgta cacgccgtgt acatcaaagg atcaagaacc     540
gggtggcaaa tgatgtccag aaactggggc caaaactggc agagcaacgc caacctcaac     600
ggccaaagcc tctcattccg ggtggtcacc ggcgacagcc gcagcgtcgt ctcctacaac     660
gccgctcccc ccggctggtc cttcggccag acctactccg gcgcccagtt ccgctag       717
```

<210> SEQ ID NO 12
<211> LENGTH: 252
<212> TYPE: PRT
<213> ORGANISM: Prunus cerasus

<400> SEQUENCE: 12

```
Met Lys Met Ala Leu Ala Tyr Gly Phe Cys Leu Val Gly Leu Leu Ala
 1               5                   10                  15

Met Val Ser Cys Ala His Ala Tyr Gly Gly Gly Trp Val Asn Ala
            20                  25                  30

Arg Ala Thr Phe Tyr Gly Gly Asp Ala Ser Gly Thr Met Gly Gly
        35                  40                  45

Ala Cys Gly Tyr Gly Asn Leu Tyr Ser Gln Gly Tyr Gly Thr Asn Thr
 50                  55                  60

Ala Ala Leu Ser Thr Ala Leu Phe Asn Asn Gly Leu Gly Cys Gly Ser
 65                  70                  75                  80

Cys Tyr Glu Ile Arg Cys Val Asn Asp Pro Lys Trp Cys Leu Pro Gly
                85                  90                  95

Ala Ile Val Val Thr Ala Thr Asn Phe Cys Pro Pro Asn Asn Ala Leu
            100                 105                 110

Pro Asn Asn Ala Gly Gly Trp Cys Asn Pro Pro Gln His His Phe Asp
        115                 120                 125

Leu Ser Gln Pro Val Phe Gln His Ile Ala Gln Tyr Lys Ala Gly Val
    130                 135                 140

Val Pro Val Ala Tyr Arg Arg Val Pro Cys Arg Arg Gly Gly Ile
145                 150                 155                 160

Arg Phe Thr Ile Asn Gly His Ser Tyr Phe Asn Leu Val Leu Ile Thr
                165                 170                 175

Asn Val Gly Gly Ala Gly Asp Val His Ser Val Ser Val Lys Gly Ser
            180                 185                 190

Arg Thr Gly Trp Gln Ala Met Ser Arg Asn Trp Gly Gln Asn Trp Gln
        195                 200                 205

Ser Asn Ser Tyr Leu Asn Gly Gln Ser Leu Ser Phe Lys Val Thr Thr
    210                 215                 220
```

```
Ser Asp Gly Arg Thr Val Val Ala Tyr Asn Ala Ala Pro Ala Gly Trp
225                 230                 235                 240

Ser Phe Gly Gln Thr Tyr Ser Gly Ala Gln Phe Arg
                245                 250

<210> SEQ ID NO 13
<211> LENGTH: 252
<212> TYPE: PRT
<213> ORGANISM: Prunus persica

<400> SEQUENCE: 13

Met Lys Met Ala Leu Ala Tyr Gly Phe Cys Leu Val Gly Leu Leu Ala
 1               5                   10                  15

Met Val Ser Cys Ala His Ala Tyr Gly Gly Gly Trp Val Asn Ala
                20                  25                  30

Arg Ala Thr Phe Tyr Gly Gly Gly Asp Ala Ser Gly Thr Met Gly Gly
            35                  40                  45

Ala Cys Gly Tyr Gly Asn Leu Tyr Ser Gln Gly Tyr Gly Thr Asn Thr
    50                  55                  60

Ala Ala Leu Ser Thr Ala Leu Phe Asn Asn Gly Leu Gly Cys Gly Ser
65                  70                  75                  80

Cys Tyr Glu Ile Arg Cys Val Ser Asp Pro Lys Trp Cys Leu Pro Gly
                85                  90                  95

Ala Ile Val Val Thr Ala Thr Asn Phe Cys Pro Pro Asn Asn Ala Leu
            100                 105                 110

Pro Asn Asn Ala Gly Gly Trp Cys Asn Pro Pro Gln His His Phe Asp
        115                 120                 125

Leu Ser Gln Pro Val Phe Gln His Ile Ala Gln Tyr Lys Ala Gly Val
    130                 135                 140

Val Pro Val Ala Tyr Arg Arg Val Pro Cys Arg Arg Arg Gly Gly Ile
145                 150                 155                 160

Arg Phe Thr Ile Asn Gly His Ser Tyr Phe Asn Leu Val Leu Ile Thr
                165                 170                 175

Asn Val Gly Gly Ala Gly Asp Val His Ser Val Ser Val Lys Gly Ser
            180                 185                 190

Arg Thr Gly Trp Gln Ala Met Ser Arg Asn Trp Gly Gln Asn Trp Gln
        195                 200                 205

Ser Asn Ser Tyr Leu Asn Gly Gln Ser Leu Ser Phe Lys Val Thr Thr
    210                 215                 220

Ser Asp Gly Arg Thr Val Val Ser Tyr Asn Ala Ala Pro Ala Gly Trp
225                 230                 235                 240

Ser Phe Gly Gln Thr Tyr Ser Gly Ala Gln Phe Arg
                245                 250

<210> SEQ ID NO 14
<211> LENGTH: 252
<212> TYPE: PRT
<213> ORGANISM: Prunus avium

<400> SEQUENCE: 14

Met Lys Met Ala Leu Ala Tyr Gly Phe Cys Leu Val Gly Leu Leu Ala
 1               5                  10                  15

Met Val Ser Cys Ala His Ala Tyr Gly Gly Gly Gly Trp Val Asp Ala
                20                  25                  30

Arg Ala Thr Phe Tyr Gly Gly Ser Asp Ala Ser Gly Thr Met Gly Gly
            35                  40                  45
```

-continued

```
Ala Cys Gly Tyr Gly Asn Leu Tyr Ser Gln Gly Tyr Gly Thr Asn Thr
     50                  55                  60

Ala Ala Leu Ser Thr Ala Leu Phe Asn Asn Gly Leu Gly Cys Gly Ser
 65                  70                  75                  80

Cys Tyr Glu Ile Arg Cys Val Asn Asp Pro Lys Trp Cys Leu Pro Gly
                 85                  90                  95

Ala Ile Val Val Thr Ala Thr Asn Phe Cys Pro Pro Asn Asn Ala Leu
            100                 105                 110

Pro Asn Asn Ala Gly Gly Trp Cys Asn Pro Pro Gln His His Phe Asp
            115                 120                 125

Leu Ser Gln Pro Val Phe Gln His Ile Ala Gln Tyr Lys Ala Gly Val
        130                 135                 140

Val Pro Val Ala Tyr Arg Arg Val Pro Cys Arg Arg Gly Gly Ile
145                 150                 155                 160

Arg Phe Thr Ile Asn Gly His Ser Tyr Phe Asn Leu Val Leu Ile Thr
                165                 170                 175

Asn Val Gly Gly Ala Gly Asp Val His Ser Val Ser Val Lys Gly Ser
            180                 185                 190

Arg Thr Gly Trp Gln Ala Met Ser Arg Asn Trp Gly Gln Asn Trp Gln
        195                 200                 205

Ser Asn Ser Tyr Leu Asn Gly Gln Ser Leu Ser Phe Lys Val Thr Thr
    210                 215                 220

Ser Asp Gly Arg Thr Val Val Ser Tyr Asn Ala Ala Pro Ala Gly Trp
225                 230                 235                 240

Ser Phe Gly Gln Thr Tyr Ser Gly Ala Gln Leu Arg
                245                 250
```

```
<210> SEQ ID NO 15
<211> LENGTH: 239
<212> TYPE: PRT
<213> ORGANISM: Capsicum annuum

<400> SEQUENCE: 15
```

```
Met Ala Leu Leu Gly Leu Leu Leu Met Gly Ile Ser Leu Met Phe Gln
  1               5                  10                  15

Ser Val His Gly Tyr Gly Gly Trp Ile Asn Ala His Ala Thr Phe Tyr
                 20                  25                  30

Gly Gly Gly Asp Ala Ser Gly Thr Met Gly Gly Ala Cys Gly Tyr Gly
             35                  40                  45

Asn Leu Tyr Ser Ser Gly Tyr Gly Thr Asn Thr Ala Ala Leu Ser Thr
     50                  55                  60

Ala Leu Phe Asn Asn Gly Leu Ser Cys Gly Gln Cys Phe Gln Leu Met
 65                  70                  75                  80

Cys Val Asn Ala Arg Gln Tyr Cys Leu Pro Gly Ile Ile Thr Val Thr
                 85                  90                  95

Ala Thr Asn Phe Cys Pro Pro Gly Gly Trp Cys Asp Pro Pro Asn His
            100                 105                 110

His Phe Asp Leu Ser Gln Pro Ile Phe Leu Arg Ile Ala Gln Tyr Arg
        115                 120                 125

Ala Gly Ile Val Pro Val Ala Tyr Arg Arg Val Pro Cys Arg Arg
    130                 135                 140

Gly Gly Ile Arg Phe Thr Ile Asn Gly His Ser Tyr Phe Asn Leu Val
145                 150                 155                 160

Leu Val Thr Asn Val Gly Gly Ser Gly Asp Val His Ser Val Tyr Ile
```

```
                        165                 170                 175
Lys Gly Ser Arg Thr Gln Trp Gln Pro Met Ser Arg Asn Trp Gly Gln
            180                 185                 190

Asn Trp Gln Asn Asn Ala Tyr Leu Asn Gly Gln Ser Leu Ser Phe Lys
        195                 200                 205

Val Thr Thr Gly Asp Gly Arg Thr Val Val Ser Tyr Asn Ala Ala Pro
    210                 215                 220

Ser Ser Trp Ser Phe Gly Gln Thr Phe Ser Gly Gly Gln Phe Arg
225                 230                 235

<210> SEQ ID NO 16
<211> LENGTH: 239
<212> TYPE: PRT
<213> ORGANISM: Lycopersicon esculentum

<400> SEQUENCE: 16

Met Ala Leu Leu Ala Ile Leu Met Gly Ile Ser Leu Met Phe Gln
 1               5                  10                  15

Ser Ala His Gly Tyr Gly Gly Trp Ile Asn Ala His Ala Thr Phe Tyr
            20                  25                  30

Gly Gly Gly Asp Ala Ser Gly Thr Met Gly Gly Ala Cys Gly Tyr Gly
        35                  40                  45

Asn Leu Tyr Ser Thr Gly Tyr Gly Thr Asn Thr Ala Ala Leu Ser Thr
    50                  55                  60

Ala Leu Phe Asn Asn Gly Leu Ser Cys Gly Ala Cys Phe Gln Leu Met
65                  70                  75                  80

Cys Val Asn Ala Gly Gln Tyr Cys Leu Pro Gly Ile Ile Thr Val Thr
                85                  90                  95

Ala Thr Asn Phe Cys Pro Pro Gly Gly Trp Cys Asp Pro Pro Arg Pro
            100                 105                 110

His Phe Asp Leu Ser Gln Pro Ile Phe Leu Arg Ile Ala Gln Tyr Arg
        115                 120                 125

Ala Gly Ile Val Pro Val Ala Tyr Arg Arg Val Pro Cys Arg Arg Ser
    130                 135                 140

Gly Gly Ile Arg Phe Thr Ile Asn Gly His Ser Tyr Phe Asn Leu Val
145                 150                 155                 160

Leu Val Thr Asn Val Gly Gly Ser Gly Asp Val His Ser Val Tyr Ile
                165                 170                 175

Lys Gly Ser Arg Thr Gln Trp Gln Pro Met Ser Arg Asn Trp Gly Gln
            180                 185                 190

Asn Trp Gln Asn Asn Ala Tyr Leu Asn Gly Gln Ser Leu Ser Phe Lys
        195                 200                 205

Val Thr Thr Gly Asp Gly Arg Thr Val Val Ser Tyr Asn Ala Ala Pro
    210                 215                 220

Ser Ser Trp Ser Phe Gly Gln Thr Phe Ser Gly Gly Gln Phe Arg
225                 230                 235

<210> SEQ ID NO 17
<211> LENGTH: 249
<212> TYPE: PRT
<213> ORGANISM: Ipomoea batatas

<400> SEQUENCE: 17

His Ser Ser Thr Asn Ser Thr Glu Ala Ile Thr Met Ala Val Leu Glu
 1               5                  10                  15

Leu Leu Leu Val Gly Val Leu Ala Thr Leu Ser Pro Val His Gly Tyr
```

-continued

```
                20                  25                  30
Trp Gly Trp Ser Ser Ala Arg Ala Thr Phe Tyr Gly Gly Asp Ala
        35                  40                  45

Ser Gly Thr Met Gly Gly Ala Cys Gly Tyr Gly Asn Leu Tyr Ser Ser
    50                  55                  60

Gly Tyr Gly Thr Asn Thr Ala Ala Leu Ser Thr Ala Leu Phe Asn Asn
65                  70                  75                  80

Gly Leu Ser Cys Gly Ser Cys Phe Gln Ile Arg Cys Val Asn Asp Arg
            85                  90                  95

Ser Cys Leu Arg Gly Val Ile Thr Val Thr Ala Thr Asn Phe Cys Pro
            100                 105                 110

Pro Gly Gly Trp Cys Glu Pro Pro Asn Pro His Phe Asp Leu Ser Gln
        115                 120                 125

Pro Val Phe Leu Arg Ile Ala Gln Tyr Arg Ala Gly Val Val Pro Val
    130                 135                 140

Ala Tyr Arg Arg Val Pro Cys Arg Arg Ser Gly Gly Ile Arg Phe Thr
145                 150                 155                 160

Ile Asn Gly His Ala Phe Phe Asn Leu Val Leu Val Thr Asn Val Gly
                165                 170                 175

Gly Ser Gly Asp Val His Ala Val Tyr Ile Lys Gly Ser Arg Thr Gly
            180                 185                 190

Trp Gln Met Met Ser Arg Asn Trp Gly Gln Asn Trp Gln Ser Asn Ala
        195                 200                 205

Asn Leu Asn Gly Gln Ser Leu Ser Phe Arg Val Val Thr Gly Asp Ser
    210                 215                 220

Arg Ser Val Val Ser Tyr Asn Ala Ala Pro Pro Gly Trp Ser Phe Gly
225                 230                 235                 240

Gln Thr Tyr Ser Gly Ala Gln Phe Arg
            245
```

US 7,687,683 B2

SWEETPOTATO EXPANSIN CDNA AND HIGH-YIELD TRANSGENIC PLANTS USING THE SAME

CROSS-REFERENCE TO RELATED PATENT APPLICATION

This application claims the benefit of Korean Patent Application No. 10-2006-0049596, filed on Jun. 1, 2006, in the Korean Intellectual Property Office, the disclosure of which is incorporated herein in its entirety by reference.

BACKGROUND OF THE INVENTION

1. Technical Field

The present invention relates to a sweetpotato expansin cDNA useful in the generation of highly productive transgenic plants. More particularly, the present invention relates to a sweetpotato expansin cDNA, a transformation vector carrying the same, and a method of preparing a transgenic plant having increased biomass and/or seed production.

2. Background Art

Since the discovery of expansin by Cosgrove and his colleagues (McQueen-Mason et al., 1992, Plant Cell 4, 1425-1433), intensive studies have been conducted thereon. In early studies, expansins were known as cell-wall-loosening enzymes that mediate, at least in part, pH-dependent extension of the plant cell wall and the growth of the cell (Cosgrove, 2000, Nature 407, 321-326). Since then, expansins were found to be in either α- or β-form (Shcherban et al., 1995, PNAS 92, 9245-9249). expansion, a variety of other plant processes, including morphogenesis (Ruan et al., 2001, Plant Cell 13, 47-60), softening of fruits (Rose et al., 2000, Plant Physiology 123, 1583-1592; Civello et al., 1999, Plant Physiology 121, 1273-1280), growth of the pollen tube (Cosgrove et al., 1997, PNAS 94, 6559-6564), elongation of graviresponding roots (Zhang and Hasenstein, 2000, Plant Cell Physiology 41, 1305-1312), and elongation of root cells (Lee et al., 2003, Plant Physiology 131, 985-997) (for review, Lee et al., 2001, Cur. Opin. Plant Biol. 4, 527-532).

Further, the expression pattern of expansins in flooded rice and tomatoes are well studied. It has been found that expansins are expressed in the shoot apical meristem of tomato for incipient leaf primordium initiation (Reinhardt et al., 1998, Plant Cell 10, 1427-1437). An expansin gene (Exp1) was cloned and found through transformants therewith to play an important role in the growth and ripening of tomato fruits (Brummell et al., 1999, Plant Cell, 11: 2203-2216). Expansin mRNA was accumulated just before the rate of growth or the loosening degree of the cell wall started to increase, suggesting that the expression of expansin genes is correlated with cell elongation (Cho and Kende, 1997a, Plant Cell 9, 1661-1671; 1997b, Plant Physiology 113, 1137-1143; 1998, Plant Journal 15, 805-812). Transgenic rice plants in which expansins are overexpressed were observed to further increase the length of cotyledons by 31-97% compared with the wildtype (Choi et al., 2003 Plant Cell, 15: 1386-1398). However, the transgenic rice plants are unable to bear seeds due to male sterility.

Increasing grain production is very important because seeds of grain plants are staple foods for most people. Since starch usually accounts for 60-70% of the weight of each grain, scientists have made extensive effort to augment the starch content of grains, thereby increasing grain production.

ADP-glucose pyrophosphylase (AGPase) is known as an allosteric enzyme which catalyzes the first committed step of starch synthesis in the plastid, converting glucose 1-phosphate and ATP to ADP-glucose and PPi and is exquisitely sensitive to allosteric regulation, with 3-phosphoglyceric acid (3PGA) acting as an activator and Pi as an inhibitor. Genes encoding this enzyme have been used in the study for enhancing starch synthesis in grains. A mutant (Sh2-Rev6) derived from maize AGPase by the addition of two amino acid residues (tyrosine and serine) corresponding to six nucleotides becomes insensitive to inhibitor of APGase and promotes starch synthesis in maize grains, increasing seed weight 11-18% (Giroux et al., 1996, PNAS 93, 5824-5829). The maize mutant AGPase (Sh2r6hs) has decreased sensitivity to the inhibitor and exhibits more stable binding between its small and large subunits. Transgenic Sh2r6hs wheat lines using a CaMV35S promoter produced on average 38% more seed weight per plant compared with wild-type (Smidansky et al., 2002, PNAS 99, 1724-1729). Transgenic Sh2r6hs rice lines using an endosperm-specific promoter (maize ubiquitin promoter) produced on average 20% more seed and plant weight compared with wild-type (Smidansky et al., 2003, Planta, 216, 656-664).

Therefore, there has been a need for transgenic plants that can remarkably increase biomass or seed production.

SUMMARY OF THE INVENTION

Accordingly, the present invention has been made keeping in mind the above problems occurring in the prior art, and an object of the present invention is to provide sweetpotato expansin (IbExpansin) cDNA with which highly productive transgenic plants can be prepared.

It is another object of the present invention to provide a plant transformation vector carrying an IbExpansin cDNA.

It is a further object of the present invention to provide a highly productive transgenic plant that comprises a vector carrying the IbExpansin cDNA.

In accordance with an aspect of the present invention, there is provided an isolated DNA fragment, comprising a nucleotide sequence of SEQ ID NO.: 1.

Preferably, the DNA fragment is a cDNA synthesized from a sweetpotato (*Ipomoea batatas* cv Jinhongmi) expansin gene (IbExpansin).

In accordance with another aspect of the present invention, there is provided a binary vector for transforming plants, comprising the DNA fragment.

Also provided is a microorganism, comprising the DNA fragment or the vector, in accordance with a further aspect of the present invention.

In a still another aspect, the present invention provides a transgenic plant, comprising the DNA fragment or the vector.

In still a further aspect, the present invention provides a PCR primer suitable for amplifying a DNA fragment comprising the nucleotide sequence of SEQ ID NO.: 1, said primer being represented by a nucleotide sequences as shown in SEQ ID NO: 5 or 6.

In yet another aspect, the present invention provides an open reading frame (ORF) of the sweetpotato expansin gene (IbExpansin), comprising a nucleotide sequence of SEQ ID NO.: 11, which ranges from nucleotide 34 to nucleotide 750 of SEQ ID NO.: 1.

In yet a further aspect, the present invention provides a binary vector for transforming plants, comprising the ORF of the sweetpotato expansin gene (IbExpansin).

In yet a still another aspect, the present invention provides a microorganism, comprising the ORF or the binary vector.

In yet still a further aspect, the present invention provides a transgenic plant, comprising the ORF or the binary vector.

In still yet another aspect, the present invention provides an isolated polypeptide, translated from the ORF, comprising an amino acid sequence of SEQ ID NO.: 2.

In a final aspect, the present invention provides a method for increasing seed production and/or biomass, comprising inserting an expansin gene into a binary vector, and introducing the binary vector into plants.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The above and other objects, features and other advantages of the present invention will be more clearly understood from the following detailed description taken in conjunction with the accompanying drawings, in which:

FIG. 4 shows comparison of the amino acid sequence of the sweetpotato expansin cDNA of the present invention, with amino acid sequences of other plant expansin cDNA;

FIG. 5 shows amino acid sequence homologies between the sweetpotato expansin cDNA of the present invention and other plant expansin cDNA;

FIG. 15 shows the comparison of seed production between an *Arabidopsis* transformant expressing the sweetpotato expansin cDNA of the present invention and the wild-type.

DETAILED DESCRIPTION OF THE INVENTION

Figure 1:
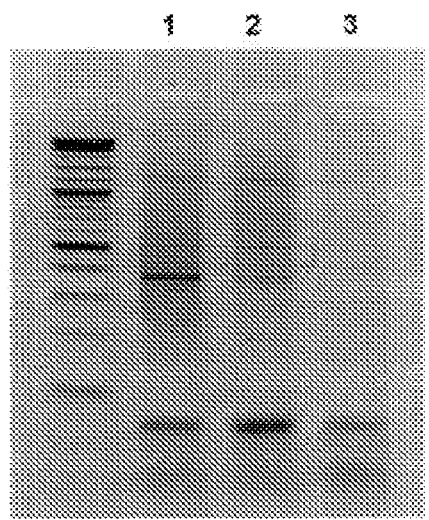
FIG. 1 is a view showing the results of primary PCR for cloning a full-length sweetpotato expansin cDNA.

In order to accomplish the objects, the present inventors succeeded in cloning a sweetpotato expansin cDNA (IbExpansin), constructing a binary vector, suitable for plant transformation, carrying the clone, and transforming the vector into *Arabidopsis*. The transgenic *Arabidopsis* was found to significantly increase in biomass, and, notably, three times in seed production.

In one aspect, therefore, the present invention provides an isolated DNA fragment, comprising a nucleotide sequence of SEQ ID NO.: 1.

The cDNA has a nucleotide sequence 1,213 bp long, consisting of 33 bp 5'-UTR, a 717 bp ORF (open reading frame; SEQ ID NO.: 11), and a 463 bp 3'-UTR.

In accordance with another aspect, the present invention provides an isolated polypeptide that has an amino acid sequence of SEQ ID NO.: 2. translated from the ORF.

In accordance with a further aspect, the present invention provides a binary vector (pIbExpansin) for transforming plants, carrying the sweetpotato (Ipomoea batatas cv Jinhongmi) expansin cDNA (IbExpansin).

The plant transformation vector is a binary vector capable of stably expressing an exogenous gene of interest in plants.

In a pMBP1 vector, the sweetpotato expansin cDNA (IbExpansin) of the present invention is located between a CaMV35S promoter and an NOS terminator. It should be understood by those skilled in the art that any other plant transformation vector can be used instead of the pMBP1 vector.

In accordance with still a further aspect, the present invention provides a transgenic *Arabidopsis* carrying the sweetpotato expansin cDNA (IbExpansin) of the present invention on a binary vector.

The binary vector may be introduced into plants using *Agrobacterium* or a gene gun. In an embodiment of the present invention, a floral dip method (Clough and Bent, 1998, Plant J.) was used for transforming *Arabidopsis*.

In addition to *Arabidopsis*, the sweetpotato expansin cDNA (IbExpansin) of the present invention may be introduced into any plant that is adapted to have increased biomass or seed production.

In accordance with still another aspect, the present invention provides a pair of primers for the PCR amplification of the sweetpotato expansin cDNA (IbExpansin) of the present invention, which are respectively represented by SEQ ID NO.: 5 and SEQ ID NO.: 6.

Further, the present invention provides a method for increasing seed production and/or biomass by inserting an expansin gene into a binary vector, and introducing the binary vector into plants. As mentioned above, some of the expansin family genes are disclosed, but nowhere has the application of expansin genes for seed production increase been mentioned in reports predating the present invention. In accordance with the present invention, various expansin genes can be introduced into plants in order to increase their biomass and/or seed production.

The present invention is directed to a sweetpotato (Ipomoea batatas) expansin cDNA (IbExpansin), which allows plants, if transformed therewith, to increase in biomass and/or seed production. Therefore, the present invention can be effectively used for the generation of highly productive plants.

A better understanding of the present invention may be obtained through the following examples, which are set forth to illustrate, but are not to be construed as the limit of the present invention.

EXAMPLE 1

Cloning of Sweetpotato Expansin cDNA

Total RNA was isolated from a fresh storage root of sweetpotato and was used to construct an EST (Expressed Sequence Tag) library. Using this library, 2,859 ESTs were cloned and deposited in the National Center for Biotechnology Information (NCBI) with NCBI Accession Nos.: BU690119-BU692977 (You et al., 2003, FEBS Letters 536, 101-105). Of them, IbExpansin (NCBI Accession No. BU691452) was found to be about 1 kb long, and was identified as a partial cDNA devoid of the start codon ATG. To obtain full length IbExpansin, PCR was performed in the presence of an IbExpansin-specific primer (SEQ ID NO.: 3) and a T3 vector primer, with the preexisting EST library of early sweetpotato storage root development serving as a template. However, no bands were visible at the position of the expected 5' full-length size (FIG. 1).

Figure 2:
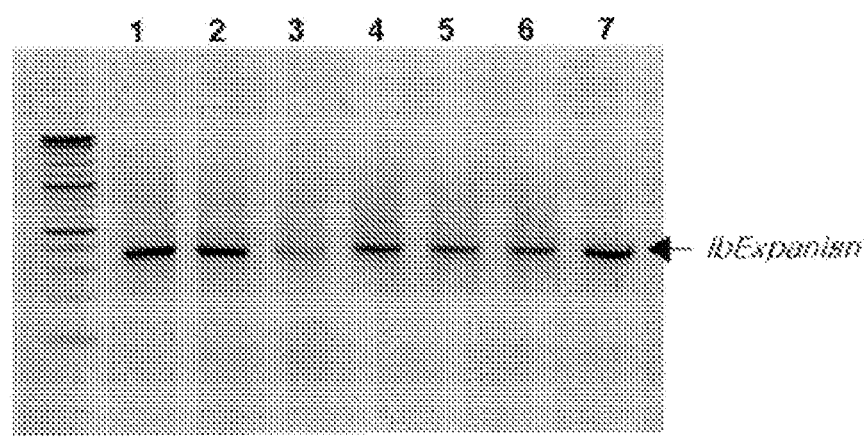
FIG. 2 is a view showing the results of secondary PCR for cloning a full-length sweetpotato expansin cDNA, with the primary PCR product serving as a template.

DNA fragments were eluted from a gel piece excised from the agarose gel at the expected full length position and was used as a template for PCR, with a set of a gene-specific nested primer (SEQ ID NO.: 4) and a T3 primer. As a result, a PCR product having a length of about 350 bp was obtained (FIG. 2).

The PCR product was inserted into a pGEM-T Easy vector for sequencing analysis and identified 5' sequence of IbExpansin.

Figure 3:
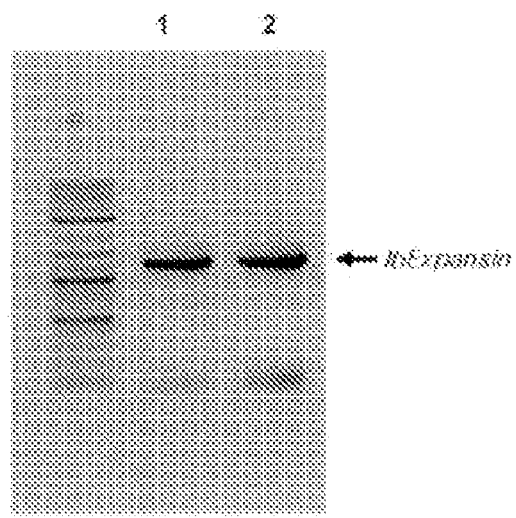
FIG. 3 is a view showing the full-length sweetpotato expansin cDNA cloned by PCR in accordance with the present invention.

On the basis of the nucleotide sequence, 5' and 3' primers were synthesized with BamHI and KpnI restriction sites provided respectively to their termini. RT-PCR was performed with the primers to obtain a full-length IbExpansin (FIG. 3).

EXAMPLE 2

Sequencing and Analysis of Nucleotide Sequence of Full-Length IbExpansin

A 1.2 kb full-length cDNA was cloned by PCR and inserted into a pGEM-T Easy vector, which was then amplified. Sequencing analysis revealed that IbExpansin is 1,213 bp long and consists of a 33 bp 5'-UTR, a 717 bp ORF, and a 463 bp 3'-UTR. This full-length IbExpansin cDNA was deposited in NCBI, with Accession No.: DQ515800). The IbExpansin amino acid sequence, consisting of 239 amino acid, is highly conserved, with the exception of the N-terminal region (FIG. 4), and shares as high as 78% homology with expansin amino acid sequences of tomato and pepper (FIG. 5).

EXAMPLE 3

Northern Blot Analysis of Tissues

1. Northern Blotting

The expression pattern of IbExpansin was examined with various tissues at various developmental stages through Northern blotting.

Figure 6:
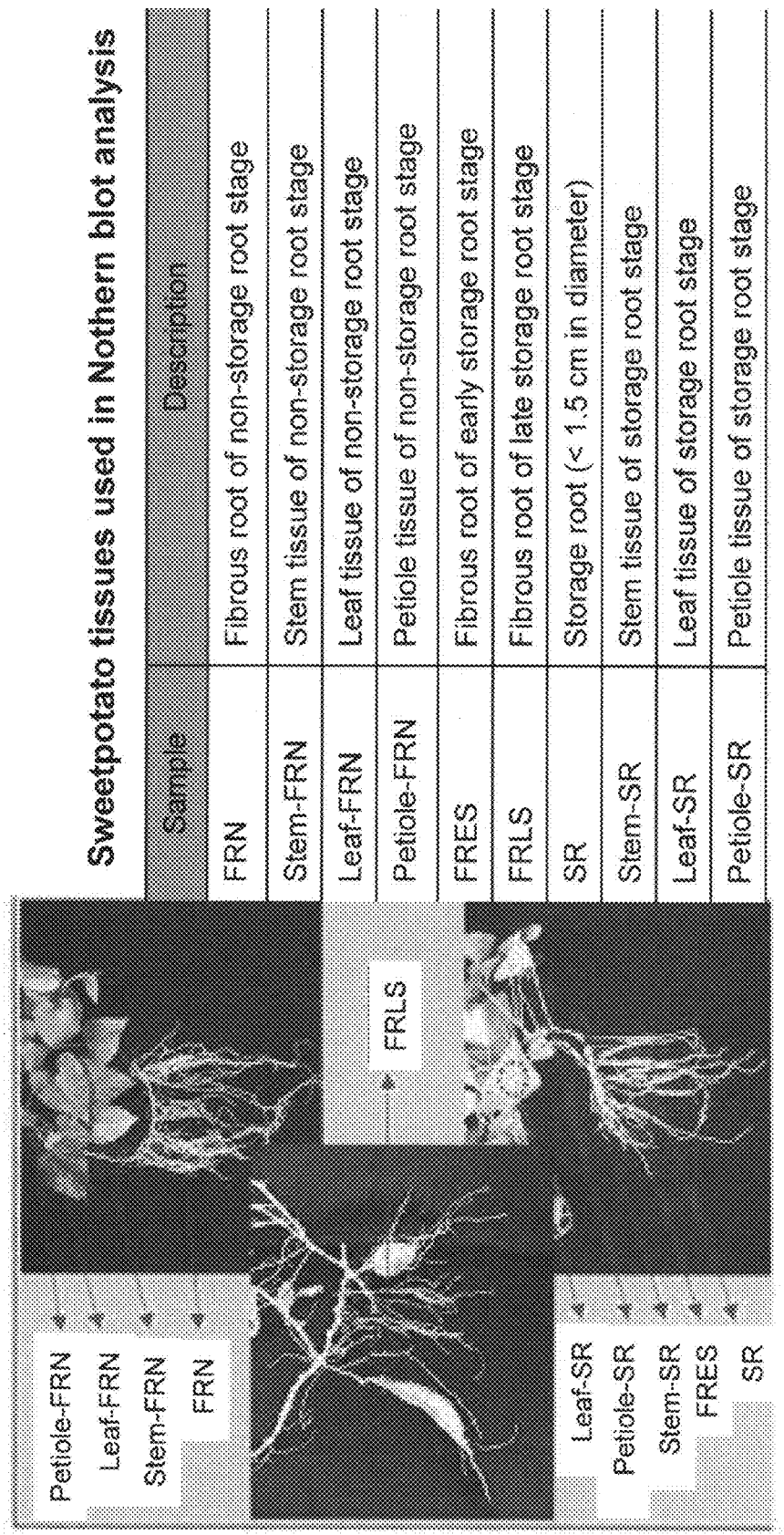
FIG. 6 shows sweetpotato tissues used in examining expression patterns of sweetpotato expansin gene of the present invention.

For the isolation of total RNA, roots, stems, leaves and petioles of sweetpotato at various developmental stages were used as RNA sources. That is, total RNA was isolated from tissues in a non-storage root stage, such as roots (FRN: fibrous root in non-storage root stage), stems (stem-FRN), leaves (Leaf-FRN) and petioles (petiole-FRN), tissues at an early storage root stage, such as roots (fibrous root in early storage root stage, FRES), tissues in a storage root stage, such as roots (SR), stems (Stem-SR), leaves (Leaf-SR) and petioles (Petiole-SR), and tissues in a late storage root stage, such as roots (fibrous root in late storage root stage, FRLS) (FIG. 6). Total RNA extraction was performed using a 4.4 M guanidinium-SDS lysis buffer (Chirgwin et al., 1979)/5.7 M CsCl gradient method (Glisin et al., 1974). About 20 μg of the extracted total RNA was electrophoresed on 1% agarose-formaldehyde gel and transferred onto a Tropilon-plus™ nylon membrane (Tropix, USA).

A probe was obtained by amplification from 2.5 ng of a plasmid carrying a 1 kb Expansin EST clone through PCR, which was performed in a PCR mixture containing 100 μM of dNTP mix exclusive of dCTP, 100 μM of dCTP-biotin, 10 μM of vector (pBluescript II) primers T3 (5'-AATTAACCCT-CACTAAAGGG-3'; SEQ ID NO.: 7) and T7 (3'-CGG-GATATCACTCAGCATAATG-5'; SEQ ID NO.: 8) each, 1×PCR buffer, and 1 unit of Taq polymerase to a final volume of 10 μl, starting with pre-denaturation at 95° C. for 5 min before 35 cycles of denaturation at 95° C. for 10 sec, annealing at 65° C. for 30 sec and extension at 72° C. for 30 sec.

The PCR-amplified biotinylated probe was purified using a QIAquick™ PCR purification kit (QIAGEN, Germany) and was added in an amount of about 100 ng onto the membrane, followed by hybridization at 65° C. for 18 hrs. The membrane was washed twice with 2×SSC/1% SDS at room temperature for 5 min, then twice with 0.1×SSC/1% SDS at room temperature for 15 min, and finally twice with 1×SSC at room temperature for 5 min. Probe detection was performed using a Southern-star™ kit (Tropix, USA). The blots were treated with a blocking buffer (1×PBS, 0.2% I-Block™ Reagent and 0.5% SDS) and labeled with alkaline phosphatase-conjugated streptavidin, followed by treatment with CDP-Star™ (Ready-to-Use). The membrane was exposed to an X-ray film (Fujifilm, Japan) for a period ranging from 10 min to 1.5 hrs.

2. Expression Pattern of IbExpansin

Figure 7:
FIG. 7 shows the expression pattern of the sweetpotato expansin gene according to the present invention.

Expression of IbExpansin was detected in the tissues in a non-storage root stage, including FRN, Stem-FRN, Leaf-FRN and Petiole-FRN, with the highest level in FRN and Petiole-FRN. However, a remarkably decreased level of expression of IbExpansin was detected in the Fibrous root of late storage root stage (FRLS), along with significantly low levels in stems and leaves at storage root-stage (FIG. 7). These expression patterns strongly imply that IbExpansin is actively expressed in tissues that are under active elongation growth.

EXAMPLE 4

Construction of Binary Vector

Figure 8:
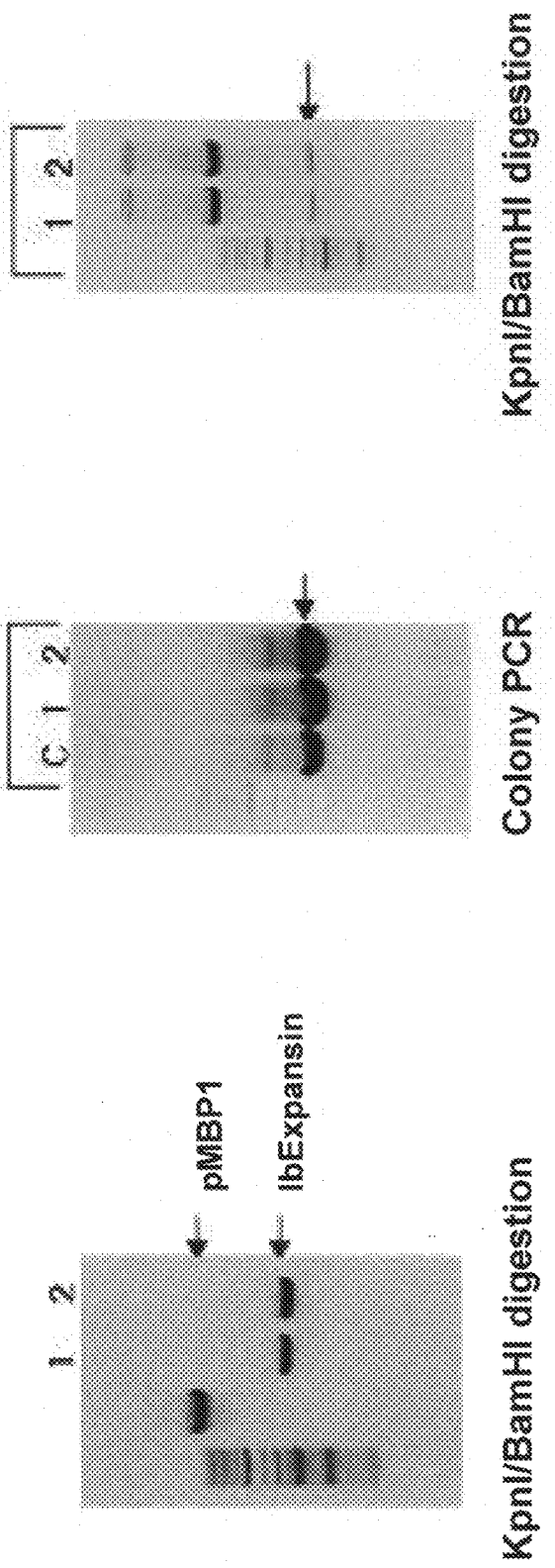
FIG. 8 shows results obtained at various process stages of constructing a binary vector for carrying the sweetpotato expansin cDNA of the present invention into *Arabidopsis*.
Figure 9:
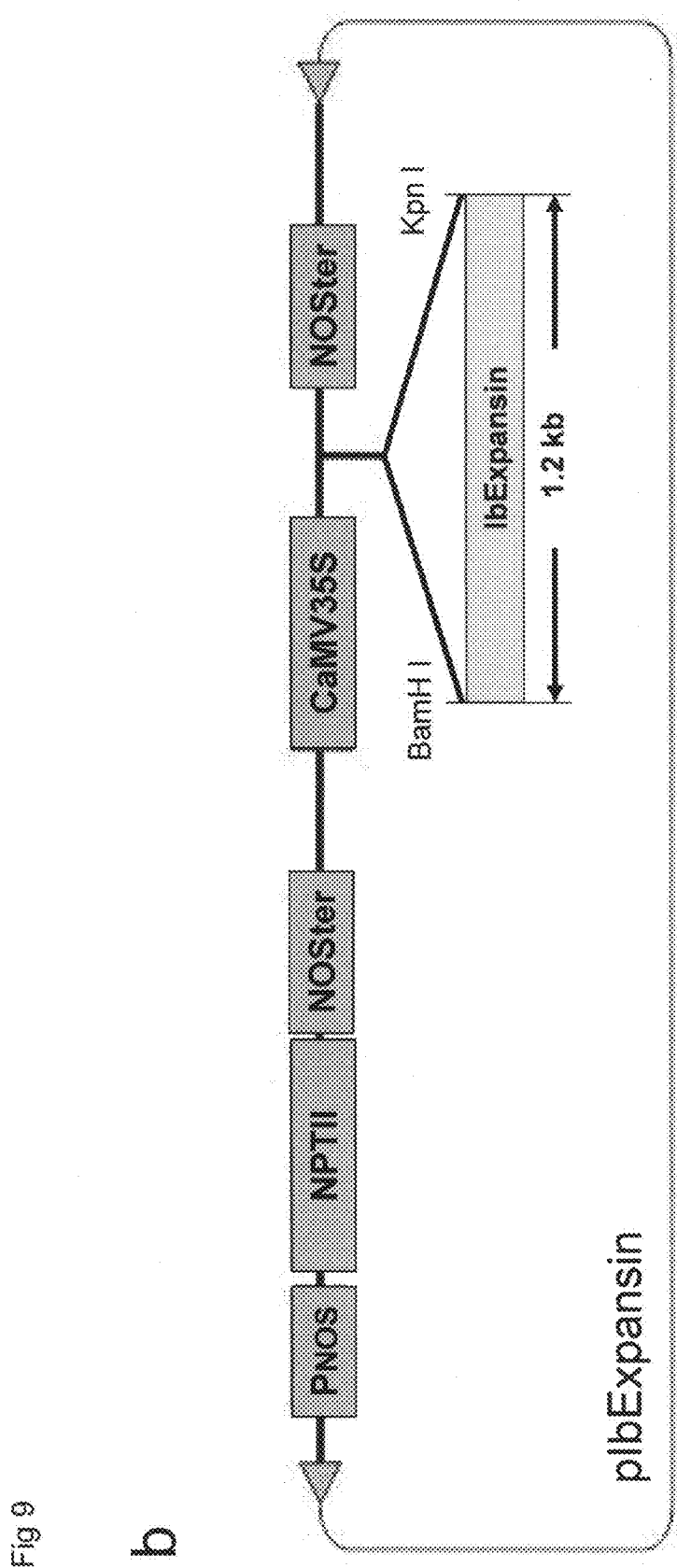
FIG. 9 is a schematic diagram showing the structure of a pIbExpansin binary vector for carrying the sweetpotato expansin cDNA of the present invention into *Arabidopsis*.

The presence of BamHI and KpnI restriction enzyme sites in the primers (SEQ ID NO.: 5 and SEQ ID NO.: 6) used for the PCR amplification of the full-length IbExpansin cDNA made it possible to digest the pGEM-T Easy vector with BamHI and KpnI to excise the cDNA therefrom. It was inserted between a CaMV35S promoter and an NOS terminator in a pMBP1 vector to construct the binary vector pIbExpansin (FIG. 9). The insertion was confirmed by colony PCR and restriction enzyme digestion (FIG. 8).

EXAMPLE 5

Transformation of pIbExpansin into *Arabidopsis*

The pIbExpansin vector constructed in Example 4 was introduced into *Agrobacterium tumefaciens* C58C1 using a freeze-thaw method (An, G. 1987, Methods in Enzymology).

The *Agrobacterium* carrying the gene of interest on the vector was cultured at 28° C. for 2 days with agitation and then brought into contact with stigma of *Arabidopsis* (*Arabidopsis thaliana* cv. *columbia*) just before flowering so as to transform the plant.

EXAMPLE 6

Screening and Identification of *Arabidopsis* Transformant

Seeds were harvested from the *Arabidopsis* transformants prepared in Example 5 and plated on tissue culture MS plates with 30 mg/L Kanamycin. Putative tranformants (T1) were transplanted into soil and used to grow T2 plants that showed a segregation ratio of 3:1 for kanamycin resistance due to the introduction of a single copy of the IbExpansin cDNA, and homozygous seeds were harvested from the T2 plants. Three lines randomly selected from the T2 plants (Exp-1, Exp-4, Exp-22) were quantitatively analyzed for the level of expression of IbExpansin.

Figure 10:
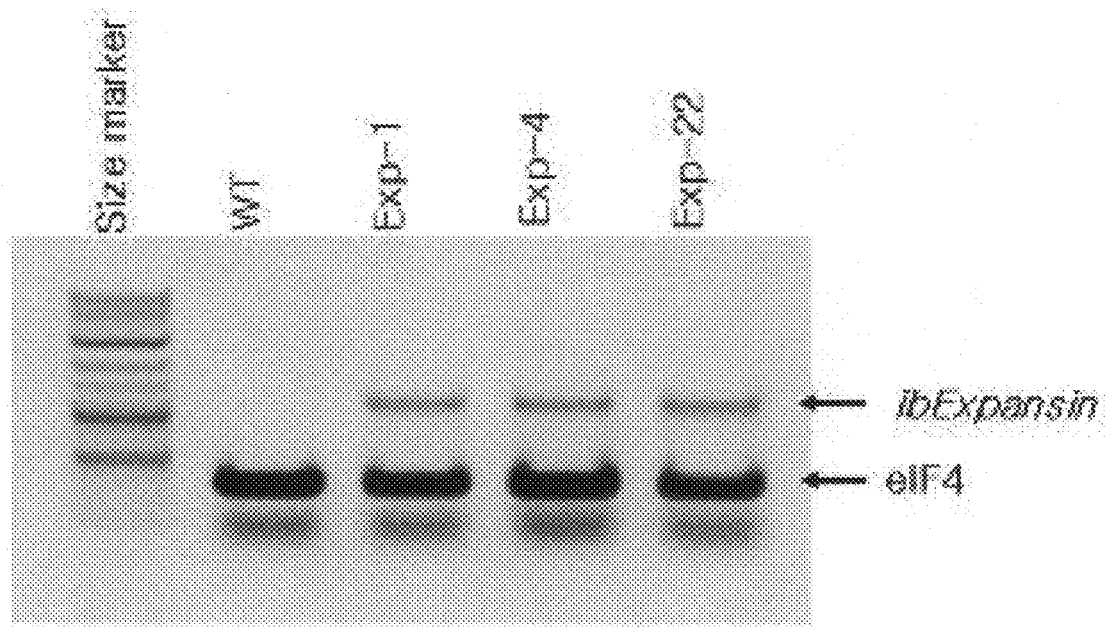
FIG. 10 shows the expression of the sweetpotato expansin cDNA of the present invention in *Arabidopsis* transformants.

For the measurement of IbExpansin expression level in the transformed *Arabidopsis*, total RNA was isolated from leaves of the transformed *Arabidopsis* with the aid of Tri-Reagent (Invitrogen, USA) and reverse-transcribed with oligo(dT) in the presence of SuperScript™ III (Invitrogen, USA). An *Arabidopsis* eIF4A1 gene was used as an internal control. RT-PCR was performed using IbExpansin-specific primers (5'-GTAGGATCCCATTCCTCTACCAATTCAACTGAA-3'; SEQ ID NO.: 5,5'-GATGGTACCACTGTCTCCACACT-CAGCATT-3'; SEQ ID NO.: 6) and eIF4A1 primers (5'-GCTCTCCCGTGGTTTCAAGGACCAGATC-3'; SEQ ID NO.: 9, 5'-GTCTGTGAGCCAATCAACCTTACGCCTG-3'; SEQ ID NO.: 10) together, starting from pre-denaturation at 94° C. for 5 min, with 30 cycles of denaturation at 94° C. for 30 sec, annealing at 58° C. for 30 sec and extension at 72° C. for 1 min, followed by a final 7-min extension at 72° C. The PCR products thus produced were separated by agarose gel electrophoresis to detect IbExpansin transcripts that did not appear in the wild-type lane (FIG. 10).

EXAMPLE 7

Growth Analysis of Transgenic *Arabidopsis*

Figure 11:
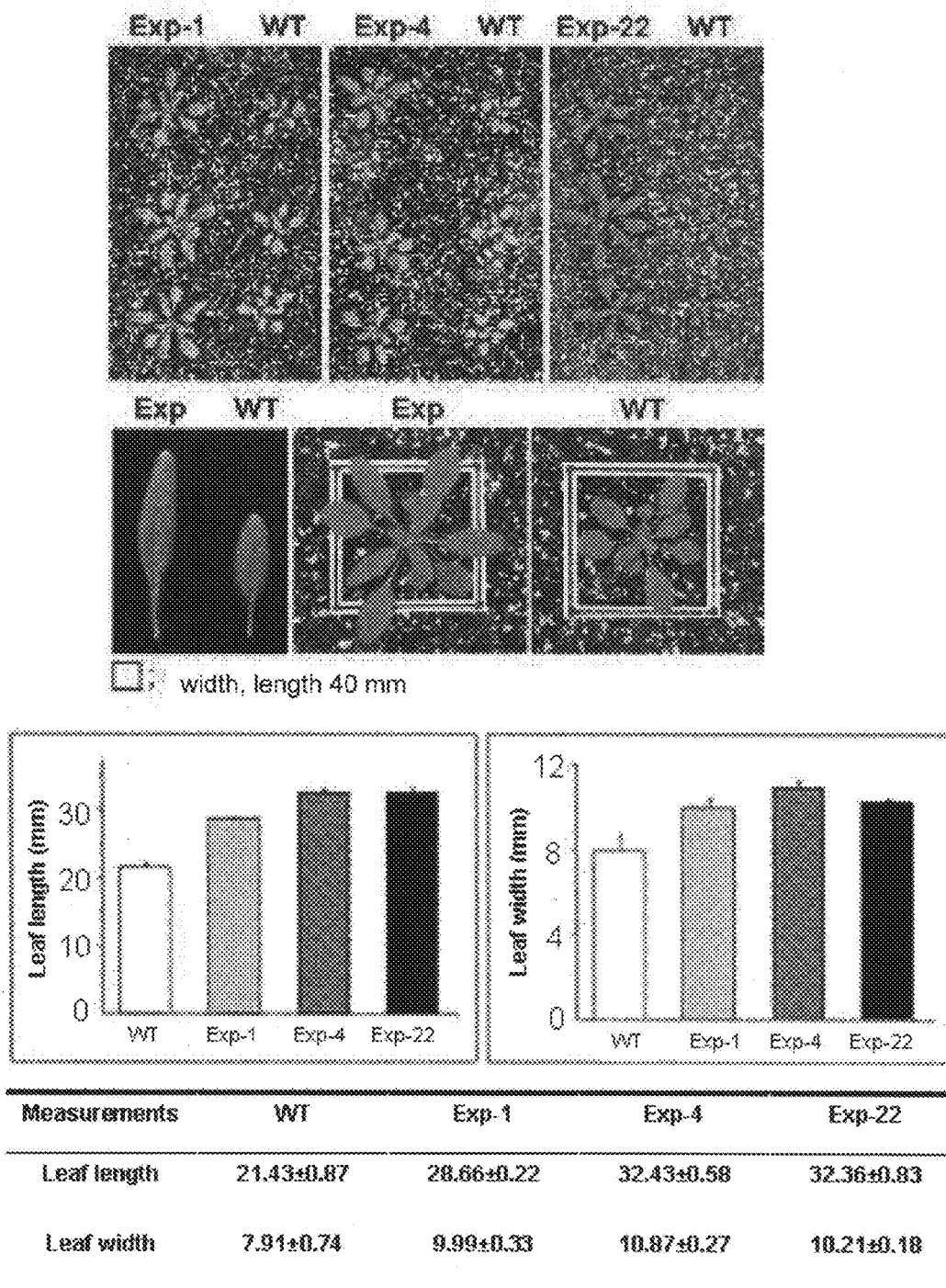
FIG. 11 shows the comparison of leaf growth between *Arabidopsis* transformants expressing the sweetpotato expansin cDNA of the present invention and the wild-type.

Growth patterns were compared between the IbExpansin *Arabidopsis* transformant and wild-type. Exp-1, Exp-4 and Exp-22 were seeded, along with wild-type, in soil and just before flower stalks arose, the leaves were compared for growth state. Exp-1, Exp-4 and Exp-22 were not different in leaf number from wild-type, but outgrew the wild-type, so that their leaves were improved in length and width compared to the wild-type (FIG. 11).

EXAMPLE 8

Analysis of Seed Production of Transgenic *Arabidopsis*

Figure 12:
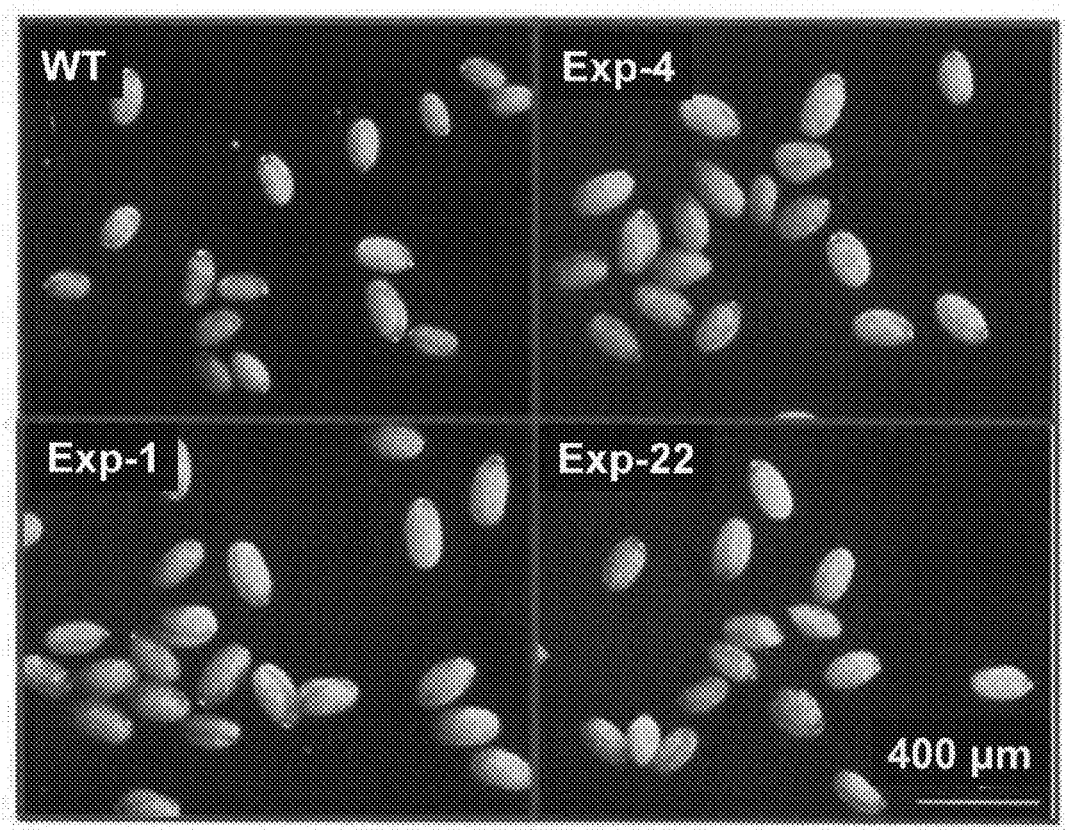
FIG. 12 shows seeds of *Arabidopsis* transformants expressing the sweetpotato expansin cDNA of the present invention and the wild-type.

Seed sizes of IbExpansin *Arabidopsis* transformants were measured and compared with the wild-type. In this regard, T3-generation homozygous seeds were used. Exp-1, Exp-4, and Exp-22 all were increased in seed size compared with the wild-type, as observed under an optical microscope (FIG. 12).

EXAMPLE 9

Analysis of Starch Content in Seed of Transgenic *Arabidopsis*

Figure 13:
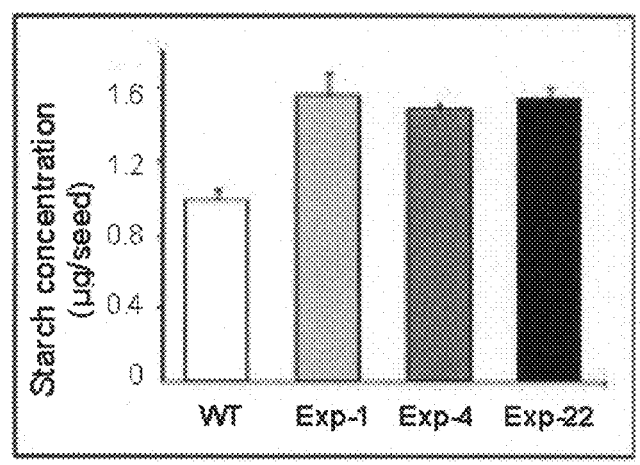
FIG. 13 shows the comparison of starch content in seeds between the *Arabidopsis* transformants expressing the sweetpotato expansin cDNA of the present invention and the wild-type.

Starch content in seeds of the IbExpansin *Arabidopsis* transformants were measured and compared with the wild-type. In this regard, T4-generation homozygous seeds were used for the *Arabidopsis* transformants and wild-type. The seeds were ground in liquid nitrogen with a pestle and mortar and 1 g of each of the ground seeds was added to 25 ml of distilled water in a 150 mL Erlenmeyer flask. The samples in distilled water were boiled for 3 min with stirring, followed by starch degradation at 135° C. for 1 hr in a sterilizer. The aqueous solutions were left at room temperature to decrease the temperature to about 60° C. Following the addition of 100 ml of distilled water, the sample solutions were analyzed for starch concentration using a Starch Assay Kit (SIGMA) according to the manufacturer's protocol. The IbExpansin *Arabidopsis* transformants had starch concentrations of 1.55±0.13 µg in one seed of Exp-1, 1.48±0.03 µg in one seed of Exp-4, and 1.54±0.06 µg in one seed of Exp-22, outweighing the wild-type (0.98±0.06 µg) (FIG. 13).

EXAMPLE 10

Analysis of Protein Content in Seed of Transgenic *Arabidopsis*

Figure 14:
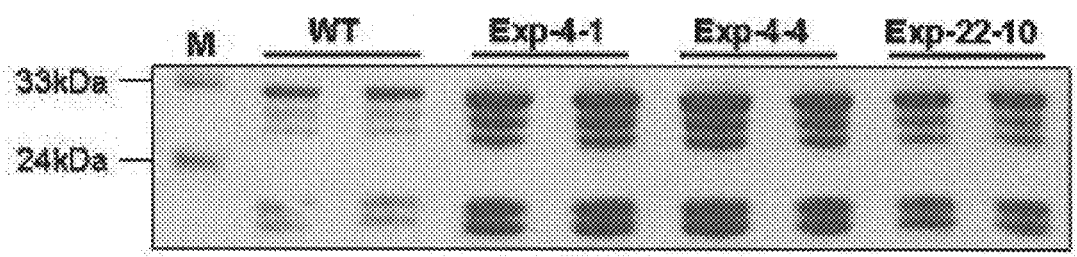
FIG. 14 shows the comparison of protein content in seed between the *Arabidopsis* transformants expressing the sweetpotato expansin cDNA of the present invention and the wild-type.

Protein contents in seeds of IbExpansin *Arabidopsis* were measured and compared with wild-type. In this regard, T3-generation homozygous seeds were used. 100 T3-generation seeds of each of the transformants and the wild-type were ground in Protein Extraction Solution (250 mM sucrose, 50 mM Tris HCl, pH 8.0, 2 mM DTT, 2 mM EDTA, Protein inhibitor Cocktail) with a drill and a plastic rod prior to centrifugation for 10 min at 4° C. at 12,000 rpm. The supernatants were transferred to new tubes and quantitatively analyzed for protein content per seed using a Protein assay kit (BioRad). All of the IbExpansin *Arabidopsis* transformants Exp-4 and Exp-22 were found to have greater protein content than the wild-type. This was confirmed by loading 2 µl of each sample in 12% SDS/polyacrylamide gel, electrophoresing and visualizing with Coomassie brilliant blue (FIG. 14).

EXAMPLE 11

Analysis of Seed Production of Transgenic Arabidopsis

The IbExpansin *Arabidopsis* transformant Exp-4 were examined for weight per 1000 seeds, silique number per plant, seed number per silique, total seed number, and total seed weight. The results are given in FIG. 13. As seen in this figure, the IbExpansin *Arabidopsis* transformant was superior to wild-type in weight per 1000 seeds, silique number per plant, seed number per silique, total seed number, and total seed weight. Consequently, seed production per plant of the IbExpansin *Arabidopsis* transformant measured 444.27±0.62 mg, which is three times heavier than 149.73±0.19 mg of wild-type (FIG. 15).

Therefore, the IbExpansin cDNA of the present invention can be applied for increasing the biomass of plants, especially for increasing the seed production of crops.

INDUSTRIAL APPLICABILITY

As described hitherto, the present invention provides an IbExpansin cDNA (expansin cDNA derived from *Ipomoea batatas* cv Jinhongmi) that is useful for transforming plants, and the resulting transgenic plants are capable of growing at higher rates than ever and increasing seed production and/or biomass greatly. Therefore, the present invention is useful in the generation of highly productive transgenic plants.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An isolated DNA molecule, consisting of the nucleotide sequence of SEQ ID NO: 1.

2. A binary vector for transforming plants, comprising the DNA molecule of claim 1.

3. A microorganism, comprising the vector of claim 2.

4. A transgenic plant, comprising the vector of claim 2.

5. An open reading frame (ORF) of the sweetpotato expansin gene (IbExpansin), consisting of the nucleotide sequence of SEQ ID NO: 11.

6. A binary vector for transforming plants, comprising the ORF of the sweetpotato expansin gene (IbExpansin) of claim 5.

7. A microorganism, comprising the vector of claim 6.

8. A transgenic plant, comprising the vector of claim 6.

* * * * *